United States Patent [19]

Ott

[11] 4,372,956

[45] Feb. 8, 1983

[54] 5,10-DIHYDROIMIDAZO[2,1-B]QUINAZOLINES AND PHARMACEUTICAL COMPOSITIONS CONTAINING THEM

[75] Inventor: Hans Ott, Pfeffingen, Switzerland

[73] Assignee: Sandoz Ltd., Basel, Switzerland

[21] Appl. No.: 207,903

[22] Filed: Nov. 18, 1980

[30] Foreign Application Priority Data

Nov. 24, 1979 [CH] Switzerland ............... 10453/79

[51] Int. Cl.³ ............... A61K 31/505; C07D 487/04
[52] U.S. Cl. ............... 424/251; 544/247; 544/250; 544/292; 564/321; 564/384; 564/389; 564/391; 564/392
[58] Field of Search ............... 544/250, 247; 424/251

[56] References Cited

U.S. PATENT DOCUMENTS

| | | | |
|---|---|---|---|
| 3,745,216 | 7/1973 | Yu-Wen Jen et al. | 424/251 |
| 3,974,165 | 8/1976 | Partyka et al. | 424/258 X |
| 4,228,167 | 10/1980 | Yamamoto et al. | 424/251 |
| 4,256,748 | 3/1981 | Chodnekar et al. | 424/251 |

FOREIGN PATENT DOCUMENTS

| | | | |
|---|---|---|---|
| 2838846 | 3/1979 | Fed. Rep. of Germany | 544/250 |
| 55/76878 | 6/1980 | Japan | 544/250 |
| 2001638 | 2/1979 | United Kingdom . | |
| 445665 | 6/1975 | U.S.S.R. | 544/250 |

OTHER PUBLICATIONS

Chen et al., J. Med. Chem. 1973, vol. 16, No. 4, pp. 407–410.

*Primary Examiner*—Donald G. Daus
*Assistant Examiner*—Diana G. Rivers
*Attorney, Agent, or Firm*—Gerald D. Sharkin; Robert S. Honor; Thomas O. McGovern

[57] ABSTRACT

A 5,10-dihydroimidazo[2,1-b]quinazoline in which at least one ring carbon atom, other than the carbon atom in the 2-position, bears a substituent, or a pharmaceutically acceptable acid addition salt thereof is a useful cardiotonic agent and vasodilator in heart insufficiency and a blood platelet aggregation inhibitor.

25 Claims, No Drawings

5,10-DIHYDROIMIDAZO[2,1-B]QUINAZOLINES AND PHARMACEUTICAL COMPOSITIONS CONTAINING THEM

This invention relates to 5,10-dihydroimidazo[2,1-b]quinazolines, their production and pharmaceutical compositions containing them.

The present invention provides 5,10-dihydroimidazo[2,1-b]quinazolines, having at least one substituted ring carbon, other than the carbon atom in the 2-position, hereinafter referred to as compounds of the invention. It is to be appreciated that the compounds of the invention are at least mono-substituted and the substitution is in any position except in position 2.

In particular the present invention provides a compound of formula I

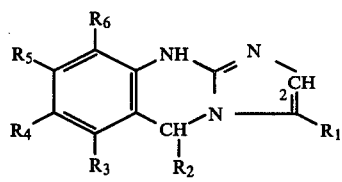

in which $R_1$ is H, $(C_{1-4})$-alkyl, phenyl or $(C_{7-11})$ phenylalkyl, the phenyl ring of the last two radicals being unsubstituted or mono- or independently di-substituted by $(C_{1-4})$-alkyl or -alkoxy or by halogen, $R_2$ is H, $(C_{1-4})$alkyl, phenyl, or phenyl mono- or independently di-substituted by $(C_{1-4})$-alkyl or -alkoxy or by halogen, and one of $R_3$ to $R_6$ is H and the remaining radicals $R_3$ to $R_6$ independently are H, $(C_{1-4})$alkyl or -alkoxy, hydroxy, halogen and if desired any two adjacent remaining radicals $R_3$ to $R_6$ represent —OCH$_2$O— with the proviso that at least one of the radicals $R_1$ to $R_6$ is other than H.

One group of compounds comprises the compounds of formula Ia

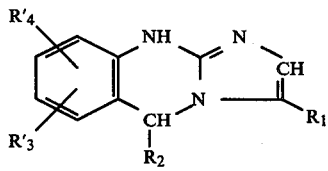

in which $R_1$ is H, $(C_{1-4})$alkyl, phenyl or $(C_{7-11})$phenylalkyl, the phenyl ring of the last two radicals being unsubstituted or mono- or independently di-substituted by $(C_{1-4})$alkyl or -alkoxy, or by fluorine, chlorine or bromine, $R_2$ is H, $(C_{1-4})$alkyl, phenyl or phenyl which is mono- or independently di-substituted by $(C_{1-4})$-alkyl or -alkoxy or by fluorine, chlorine or bromine, $R'_3$ and $R'_4$ are H, $(C_{1-4})$-alkyl or -alkoxy, fluorine, chlorine or bromine, or $R'_3$ and $R'_4$ together signify —OCH$_2$O— and at least one of the radicals $R_1$, $R_2$, $R_3'$ or $R_4'$ is other than H.

Another group of compounds comprises the compounds of formula I, wherein $R_1$ is H, $R_2$ is H, $(C_{1-4})$alkyl, or phenyl, the one, two or three radicals from $R_3$ to $R_6$ are hydrogen and the remainder of $R_3$ to $R_6$ are hydrogen, $(C_{1-4})$alkyl or -alkoxy, hydroxy, halogen and if desired any adjacent remaining radicals are —O—CH$_2$—O—, and at least one of the radicals $R_1$ to $R_6$ is other than H. In the formulae I and Ia the phenyl ring ring of the tricyclic nucleus is preferably substituted, especially in position 6, 7 or 8. This phenyl ring is preferably di-substituted, especially in positions 6, 7 and/or 8, and particularly substituted in positions 7 and 8. As a substituent $(C_{1-4})$-alkyl or -alkoxy or —O—CH$_2$—O— is preferred, especially methyl, methoxy or —OCH$_2$O—. $(C_{1-4})$-alkyl or -alkoxy preferably has 2 or 1, and especially 1, carbon atom. Alkyl in the phenylalkyl radical preferably has 2 or 1, and especially 1, carbon atom. As halogen, fluorine, bromine or chlorine are preferred.

The compounds of the invention may exist in tautomeric forms e.g. as the 1,5-dihydroimidazo[2,1-b]quinazolines, in particular of formula I'.

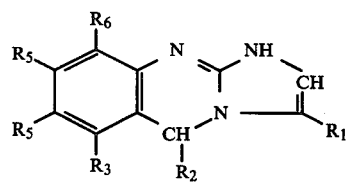

Although for the sake of simplicity reference is only made herein, and the nomenclature used herein refers to only one particular form, i.e. to the 1,5-dihydroimidazo[2,1-b]quinazolines, it is to be understood that the compounds of the invention are not limited to these forms.

The present invention in another aspect provides a process for the production of a compound of the invention, characterized in that a corresponding 2-amino-3-(2,2-dialkoxyethyl)-3,4-dihydro-quinazoline is hydrolysed.

In particular a compound of formula I may be produced by hydrolysing a corresponding compound of formula II,

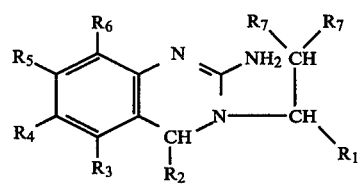

in which $R_1$ to $R_6$ are as defined above and the groups $R_7$ are independently $(C_{1-4})$alkoxy.

The process may be effected in conventional manner for the hydrolysis of analogous acetals with ring cyclisation, especially under acid conditions, e.g. with an aqueous mineral acid, such as hydrochloric acid. An organic solvent may be present. The reaction is conveniently effected at from room temperature to the reflux temperature.

The 2-amino-3-(2,2-dialkoxyethyl)-3,4-dihydroquinazoline may be produced by reacting an appropriate N-(2,2-dialkoxyethyl)-2-amino-benzylamine with a cyanogen halide. In particular a compound of formula II may be produced by reacting a compound of formula III,

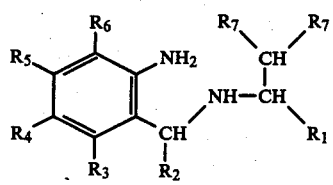

in which $R_1$ to $R_7$ are as defined above, with a cyanogen halide. The reaction may be effected in conventional manner for analogous 3,4-dihydroquinazoline synthesis.

The isolation and purification of the reaction products may take place by known methods. However the compound of formula II is conveniently not isolated, but reacted in crude form further.

The N-(2,2-dialkoxyethyl)-2-aminobenzylamines may be produced in several stages, which can be illustrated by the following scheme for the compounds of formula III, starting with compounds of formula VI or IX, which are known or can be obtained by methods known per se:

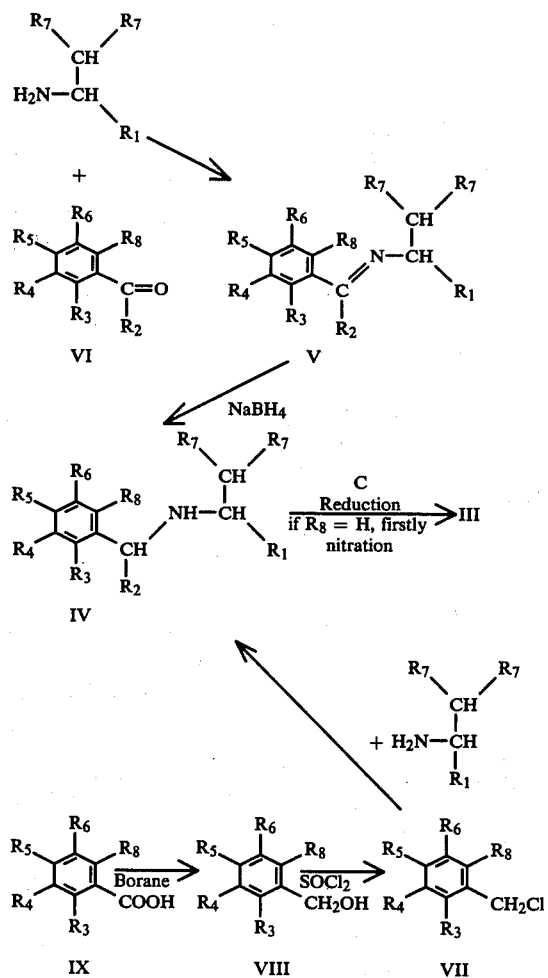

In the reaction scheme is $R_8$ H, $NO_2$ or $NHR_9$, in which $R_9$ is an amino group protecting radical, particularly an optionally substituted benzene sulfonic acid, e.g. p-toluene sulfonic acid, and $R_1$ to $R_7$ are as defined above.

Insofar as the preparation of any particular starting material is not particularly described, this is known or may be made in known manner or in a manner analogous to the processes mentioned herein.

Free base forms of the compounds of the invention and of basic starting materials e.g. of formula II or III may be converted into acid addition salt forms in conventional manner and vice versa. Suitable acids for salt formation include hydrochloric acid, fumaric acid, and oxalic acid.

In the following examples all temperatures are in degrees Centigrade and are uncorrected.

EXAMPLE 1:
5,10-dihydro-7-methylimidazo-[2,1-b]guinazoline (starting from a compound of formula IX)

(a) 5-methyl-2-nitrobenzylalcohol (VIII)

60 ml of borane-dimethyl sulphide complex are added over the course of 30 minutes to a boiling solution of 100 g of 5-methyl-2-nitrobenzoic acid in 750 ml of tetrahydrofuran. The reaction solution is boiled for 4 hours under reflux conditions. Then, 200 ml of methanol are added with cooling, and the solution is left to stand for 30 minutes at room temperature. It is then evaporated in a vacuum until dry and the residue thus obtained is partitioned between chloroform and sodium carbonate solution. The organic phase is washed with water, dried over sodium sulphate and evaporated, whereupon the heading compound is obtained as a crystalline solid having a low melting point.

(b) 5-methyl-2-nitrobenzylchloride (VII)

The above reaction product obtained in step (a) is mixed with 600 ml of benzene and 60 ml of thionyl chloride, and left to stand for 18 hours at room temperature. The reaction solution is concentrated and subsequently partitioned between benzene and ice-water. After the organic phase is washed, dried and evaporated, the heading compound remains as an orange, semi-crystalline crude product, which is used in step (c) without further purification.

(c)
N-(2,2-dimethoxyethyl)-2-nitro-5-methyl-benzylamine (IV)

A solution of 43 g of 5-methyl-2-nitrobenzyl chloride in 200 ml of ethanol is added drop-wise to a solution of 40 g of aminoacetaldehyde dimethylacetal and 40 g of triethylamine in 300 ml of ethanol at reflux temperature, and the solution is heated for 18 hours at reflux. It is then evaporated in a vacuum until dry and the residue is dissolved in ethyl acetate, and extracted several times with water. After the organic phase is dried and evaporated, the heading compound remains as a reddish oil.

(d)
N-(2,2-dimethoxyethyl)-2-amino-5-methyl-benzylamine (III)

The crude aminoacetal obtained in step (c) is dissolved in 700 ml of ethanol and is hydrogenated at room temperature and at atmospheric pressure, in the presence of 3 g of palladium catalyst (10% Pd on carbon). After the catalyst is filtered off and the filtrate evaporated, the heading compound remains as an orange oil, which is converted into the hydrochloride using methanolic hydrochloric acid.

(e) 5,10-dihydro-7-methylimidazo-[2,1-b]quinazoline (I)

45 g of N-(2-amino-5-methylbenzyl)-aminoacetaldehydedimethylacetal obtained in step (d) and 25 g of cyanogen bromide are heated under reflux in 500 ml of 95% ethanol for 18 hours. After the mixture containing 2-amino-3-(2,2-dimethoxyethyl)-6-methyl-3,4-dihydroquinazoline is cooled, 200 ml of 5 N hydrochloric acid are added, and the solution is left to stand for 2 hours at room temperature. After the reaction solution is concentrated in a vacuum, it is made alkaline with dilute caustic soda, whereupon the title compound crystallizes out, and is recrystallised from methanol or ethanol. M.p. 265° C.

EXAMPLE 2:
5,10-dihydro-7,8-dimethoxyimidazo[2,1-b]quinazoline (starting from a compound of formula VI)

(a)
3,4-dimethoxy-N-(2,2-dimethoxyethyl)-benzaldehydimine (V)

3.3 g of veratrum aldehyde and 2.1 g of aminoacetaldehyde dimethylacetal are boiled under reflux for 20 hours in 50 ml of methylene chloride, and then evaporated in a vacuum until dry. The heading compound is obtained as a yellow oil and is used in the next stage without further purification.

(b) N-(2,2-dimethoxyethyl)-3,4-dimethoxy-benzylamine (IV)

5.2 g of 3,4-dimethoxy-N-(2,2-dimethoxyethyl)-benzaldehydoxime are heated for 3 hours at reflux in 100 ml of ethanol with 0.8 g of sodium borohydride. The excess NaBH$_4$ is destroyed with a little acetone. The reaction solution is evaporated in a vacuum until dry, and the residue obtained is partitioned between methylene chloride and water. After drying and evaporating the organic solvent, an organic oil remains. The hydrochloride of the heading compound is crystallised from ethanolic hydrochloric acid as white crystals, with a m.p. of 99°–100°.

(c)
N-(2,2-dimethoxyethyl)-2-nitro-4,5-dimethoxy-benzylamine (IV)

2.2 g of these crystals are stirred for 2 hours at 0° in 5 ml of 62% nitric acid. This reaction solution is poured onto 30 ml of 2 N caustic soda and ice, and the precipitated oily product is extracted with methylene chloride. The red oil which remains after drying and evaporating the solvent is dissolved in ethanol, and then oxalic acid is added. The hydrogen oxalate of N-(2,2-dimethoxyethyl)-2-nitro-4,5-dimethoxy-benzylamine is produced as beige crystals having a m.p. of 162°–163°.

(d)
N-(2,2-dimethoxyethyl)-2-amino-4,5-dimethoxy-benzylamine (III)

1.2 g of N-(2,2-dimethoxyethyl)-2-nitro-4,5-dimethoxybenzylamine are dissolved in 20 ml of ethanol, and then hydrogenated at room temperature and at normal pressure, in the presence of 300 mg of palladium catalyst (10% on carbon). After filtering off the catalyst and evaporating the filtrate, the heading compound remains as an almost colourless oil, which is used in the next stage (e) without further purification.

(e)
5,10-dihydro-7,8-dimethoxyimidazo-[2,1-b]quinazoline (I)

1.1 g of N-(2,2-dimethoxyethyl)-2-amino-4,5-dimethoxybenzylamine and 0.5 g of cyanogen bromide are heated under reflux over-night in 10 ml of 95% ethanol. 5 ml of 5 N hydrochloric acid are then added, and the solution is left to stand at room temperature for 2 hours. After the reaction solution is concentrated in a vacuum it is made alkaline with dilute caustic soda. The little compound is obtained in crystalline form, and is crystalised from ethyl acetate. M.p. 215°–217° (from ethanol).

EXAMPLE 3:
5,10-dihydro-5-methylimidazo[2,1-b]quinazoline (I)

(a) o-tolylsulfonylaminoacetophenone (VI)

25 g of o-aminoacetophenone and 40 g of p-toluene sulfonyl chloride are together dissolved in 150 ml of pyridine and are left to stand at 50°–60° for one hour. The reaction mixture is then added to 1 liter of a stirred ice-water mixture and extracted with methylene chloride after half an hour.

The organic phase is washed several times with dilute hydrochloric acid and then with dilute sodium bicarbonate solution, dried with sodium sulphate and concentrated, affording the title compound. M.p. 142°–143°.

(b)
N-(2,2-dimethoxyethyl)-o-tolylsulfonylaminoacetophenone imine 33.8 g of o-tolylsulfonylaminoacetophenone, 13.7 g of aminoacetaldehyde dimethylacetal and 0.4 g of toluenesulfonic acid in 400 ml of toluene are boiled for 4 hours in a water separator and concentrated to dryness in vacuo.

The so obtained heading compound is used in the next step (c) without further purification.

(c)
N-(2,2-dimethoxyethyl-α-methyl-o-tolylsulfonylamino benzylamine (IV)

To a solution of 26 g of N-(2,2-dimethoxyethyl)o-tolylsulfonylamino-acetophenone imine in 250 ml of methanol 3 g of sodium borohydride are added portionwise within 15 minutes. The reaction mixture is stirred at room temperature for 30 minutes and concentrated to dryness in vacuo. The residue is partitioned between ethyl acetate and 2 N hydrochloride acid, affording the hydrochloride of the heading compound in crystalline form. M.p. 202°.

(d)
N-(2,2-dimethoxyethyl)-α-methyl-o-aminobenzylamine (III)

To 6.7 g of N-(2,2-dimethoxyethyl)-α-methyl-o-tolyl-sulfonylamino benzylamine in 150 ml of liquid NH$_3$, 1.6 g finely divided sodium are added portionwise.

After 30 minutes, 5 g of ammonium chloride are added and the reaction mixture is concentrated to dryness. The residue is taken up in methylene chloride and washed twice with water.

After the organic solvent is dried and evaporated, the title compound is obtained as a yellow oil, which is used in the following stage without further purification.

(e) 5,10-dihydro-5-methylimidazo[2,1-b]quinazoline (I)

4 g of crude N-(2,2-dimethoxyethyl)-α-methyl-o-amino-benzylamine and 1.9 g cyanogen bromide are reacted and the product is worked up in the same manner as in Example 1e to afford the heading compound. M.p. 171°–172° (crystallisation from ethanol).

In an analogous manner to that described in the foregoing Examples the following compounds are prepared:

Compounds of formula I

| Example | $R_1$ | $R_1$ | $R_3, R_4, R_5, R_6$ | m.p.[1] | Crystallised from |
|---|---|---|---|---|---|
| 4 | H | H | 9-$CH_3$ | 208–210° | ethanol |
| 5 | H | H | 6-$CH_3$ | 205–208° | ethylacetate |
| 6 | H | H | 6-Cl | 235–238° | methanol |
| 7 | H | H | 7-Cl | 278–280° | methanol |
| 8 | H | H | 7,8,9-tri-$CH_3O$ | 187–188° | methanol |
| 9 | H | H | 8-Cl | 255–257° | methanol |
| 10 | H | H | 7,9-di-$CH_3$ | 250° | methanol |
| 11 | H | H | 8,9-di-$CH_3$ | 215° | methanol |
| 12 | H | H | 9-$CH_3O$ | 175–177° | ethanol |
| 13 | H | H | 7,8-$OCH_2O$— | 268–270° | ethanol |
| 14 | H | H | 7-$CH_3O$— | 266–268° | methanol/methylene-chloride |
| 15 | H | H | 6-$CH_3O$— | 220–223° | methanol |
| 16 | H | H | 8-$CH_3O$— | 206–207° | methanol/water |
| 17 | H | H | 7,8-di-OH | 325° | methanol/water |
| 18 | H | H | 9-OH | 245–250° | methanol/methylene-chloride |
| 19 | H | H | 7-OH | 275–278° | methanol/ether |
| 20 | H | Phenyl | H | 263° | methanol |
| 21 | H | $CH_3$ | H | 171–172° | methanol |

[1]free base form.

In an analogous manner to that disclosed in the foregoing Examples, the following compounds of formula I may be prepared:

Compounds of formula I

| Example | $R_1$ | $R_2$ | $R_3, R_4, R_5, R_6$ |
|---|---|---|---|
| 22 | $CH_3$ | H | H |
| 23 | $CH_3$ | phenyl | H |
| 24 | $CH_3$ | $C_2H_5$ | 7,8-di-$OCH_3$ |
| 25 | phenyl | H | H |
| 26 | benzyl | H | H |
| 27 | o-tolyl | H | H |
| 28 | m-methoxy-phenyl | H | H |
| 29 | p-Br—phenyl | H | H |
| 30 | H | m-tolyl | H |
| 31 | H | p-methoxyphenyl | H |
| 32 | H | p-Cl—phenyl | H |
| 33 | 2-$C_2H_5$,6-$OC_2H_5$-phenyl-$(CH_2)_5$— | 2-$C_2H_5$,6-$OC_2H_5$-phenyl | H |

In a 1st group of compounds $R_1$ is H,
In a 2nd group of compounds $R_1$ is alkyl,
In a 3rd group of compounds $R_1$ is optionally substituted phenyl,
In a 4th group of compounds $R_1$ is optionally substituted phenylalkyl,
In a 5th group of compounds $R_2$ is H,
In a 6th group of compounds $R_2$ is alkyl,
In a 7th group of compounds $R_2$ is optionally substituted phenyl,
In an 8th group of compounds two of $R_3$ to $R_6$ is —O—$CH_2$—O—,
In a 9th group of compounds none of $R_3$ to $R_6$ is —O—$CH_2$—O—.

The compounds of the invention possess pharmacological activity in animals and are therefor useful as pharmaceuticals, i.e. for therapy. In particular, the compounds of the invention are useful as cardiotonic agents and vasodilators e.g. in the treatment of heart insufficiency, as indicated in the following standard tests:

Cats of 1.7 to 4 kg of body weight are narcotized (i.p.) with 40 mg/kg Nembutal. After cannulation of their Trachea, 20 mg/kg of Suxamethonium chloride (muscle relaxant) are administered and the cats are immediately artificially respirated. The brain and the spinal marrow are then destroyed with a metal bar, the cervical sympathetic trunk and the vagal nerve are disconnected.

The blood pressure of the *Arteria femoralis sinistra* is registered by a Stathum-transducer and recorded. The registration of the heart frequency is electronically derived from the systolic-diastolic blood pressure oscillations. The contractile force of the heart is recorded with a strain gauge, connected to the right ventricle in the opened thorax.

The administration of the compound of the invention is effected every 15 minutes in increasing quantities into the *Vena femoralis sinistra*.

After intravenous administration of 0.1 to 10 mg/kg of the compounds, a cardiotonic effect is observed from an increase of the contractile force of the heart. Cats of 2–4 kg body weight are narcotised with chloralose urethane (43 and 430 mg per kg body weight), tracheotomised and artificially respirated. A final expiratory pressure of 2 mm Hg is thus maintained.

The femoral artery and vein are catheterised. By effecting a thoracotomy in the 4th intercostal space, the aorta is exposed, so that an electromagnetic probe can be applied to this vessel in order to measure the blood flow. The flow signal thus obtained is electronically integrated and similarly electronically differentiated, so that the average flow through the aorta is obtained.

The phased and the average blood pressure are recorded by the catheter in the femoral artery. A vasodilatising effect of the medicaments may be established by calculating the quotient of the average blood pressure and the average flow through the aorta, or the reciprocal value thereof. These values approximately illustrate the peripheral resistance or the conductance of the peripheral vessels, and are used to judge a vasodilatising effect.

The test compound may be dispensed intravenously by means of the above-mentioned vein catheter, or may be injected into the duodenum by a small median laparatomy.

By this method, an increase in the peripheral conductance of the vascular system is found, which indicates the vasodilatising effect.

For the above mentioned use the dosage will, of course, vary depending on the compound employed, mode of administration and therapy desired. However, satisfactory results are obtained with a daily dosage from about 0.1 to about 50 mg/kg animal body weight, conveniently given in divided doses 2 to 4 times a day or in sustained release form. For the larger mammals, the total daily dosage is in the range from about 50 to about 500 mg and dosage forms suitable for oral administration comprise from about 12 to 250 mg of the compounds admixed with a solid or liquid pharmaceutical carrier or diluent.

Additionally the compounds of the invention are useful as blood aggregation inhibitors, e.g. for the treatment of thrombosis, as indicated in standard tests. For example the inhibition of blood platelet aggregation induced in vitro by adenosine diphosphate and collagen in blood platelet-rich rabbit plasma is observed with concentrations of about 1 to 25 $\mu$M of the compounds.

For the above-mentioned use, the dosage will of course vary depending on the compound employed, mode of administration and therapy desired.

However satisfactory results are obtained with a daily dosage from about 0.1 to 10 mg/kg of animal body weight, conveniently given in divided doses 2 to 4 times a day or in sustained release form.

For larger mammals, the total daily dosage is in the range from 10 to 500 mg and dosage forms suitable for oral administration comprise from about 3 to 250 mg of the compounds admixed with a solid or liquid pharmaceutical carrier or diluent. The compounds of the invention may be administered in pharmaceutically acceptable acid addition salt form. Such acid addition salt forms exhibit the same order of activity as the free base forms. The present invention also provides a pharmaceutical composition comprising a compound of the invention, in free base form or in pharmaceutically acceptable acid addition salt form, in association with a pharmaceutical carrier or diluent. Such compositions may be in the form of, for example, a solution or a tablet.

The cardiotonic and vasodilating activity is the preferred utility. The preferred compounds are the compounds of Examples 2, 13 and 5.

The compounds of Example 2, 13 and 15 have been found to be active at about 0.3–10, 0.03–3 and 0.1–10 respectively mg/kg i.v. in the above mentioned cardiotonic test.

I claim:

1. A compound of formula I

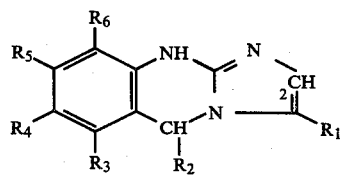

in which
$R_1$ is H, $(C_{1-4})$alkyl, phenyl or $(C_{7-11})$ phenylalkyl, the phenyl ring of the last two radicals being unsubstituted or mono- or independently di-substituted by $(C_{1-4})$alkyl or -alkoxy or by halogen,
$R_2$ is H, $(C_{1-4})$alkyl, phenyl or phenyl, mono- or independently di-substituted by $(C_{1-4})$alkyl or -alkoxy or by halogen and one of
$R_3$ to $R_6$ is H and the remaining radicals $R_3$ to $R_6$ independently are H, $(C_{1-4})$alkyl or -alkoxy, hydroxy, halogen and if desired any two adjacent remaining radicals $R_3$ to $R_6$ represent —OCH$_2$O—
with the proviso that at least one of the radicals $R_1$ to $R_6$ is other than H or pharmaceutically acceptable acid addition salt form.

2. A compound of claim 1 of formula Ia,

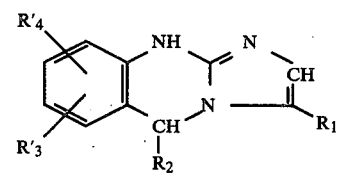

in which
$R_1$ is H, $(C_{1-4})$alkyl, phenyl or $(C_{7-11})$phenylalkyl, the phenyl ring of which is the last two radicals being unsubstituted or mono- or independently di-substituted by $(C_{1-4})$alkyl or -alkoxy or by fluorine, chlorine or bromine,
$R_2$ is H, $(C_{1-4})$alkyl, phenyl or phenyl which is mono- or independently di-substituted by $(C_{1-4})$alkyl or -alkoxy or by fluorine, chlorine or bromine,
$R_3'$ and $R_4'$ are H, $(C_{1-4})$alkyl or -alkoxy, fluorine chlorine or bromine, or
$R_3'$ and $R_4'$ together signify —OCH$_2$O— and at least one of the radicals $R_1$, $R_2$, $R_3'$ or $R_4'$ is other than H.

3. A pharmaceutical composition useful in treating heart insufficiency, inducing a cardiotonic or vasodilating effect or inhibiting blood platelet aggregation which comprises a compound of claim 1 in association with a pharmaceutical carrier or diluent.

4. A method of treating heart insufficiency, including a cardiotonic or vasodilating effect or inhibiting blood platlet aggregation, which comprises administering a therapeutically effective amount of a compound of claim 1 to a subject in need of such treatment.

5. A compound of claim 1 which is 5,10-dihydro-7,8-dimethoxyimidazo[2,1-b]quinazoline or a pharmaceutically acceptable salt thereof.

6. A compound of claim 1, which is 5,10-dihydro-7,8-methylenedioxyimidazo[2,1-b]quinazoline or a pharmaceutically acceptable salt thereof.

7. The compound of claim 1, which is 5,10-dihydro-7-methylimidazo[2,1-b]quinazoline or a pharmaceutically acceptable salt thereof.

8. The compound of claim 1, which is 5,10-dihydro-5-methylimidazo[2,1-b]quinazoline or a pharmaceutically acceptable salt thereof.

9. The compound of claim 1, which is 5,10-dihydro-9-methylimidazo[2,1-b]quinazoline or a pharmaceutically acceptable salt thereof.

10. The compound of claim 1, which is 5,10-dihydro-6-methylimidazo[2,1-b]quinazoline or a pharmaceutically acceptable salt thereof.

11. The compound of claim 1, which is 5,10-dihydro-6-chloro-imidazo[2,1-b]quinazoline or a pharmaceutically acceptable salt thereof.

12. The compound of claim 1, which is 5,10-dihydro-7-chloro-imidazo[2,1-b]quinazoline or a pharmaceutically acceptable salt thereof.

13. The compound of claim 1, which is 5,10-dihydro-7,8,9-trimethoxyimidazo[2,1-b]quinazoline or a pharmaceutically acceptable salt thereof.

14. The compound of claim 1, which is 5,10-dihydro-8-chloro-imidazo[2,1-b]quinazoline or a pharmaceutically acceptable salt thereof.

15. The compound of claim 1, which is 5,10-dihydro-7,9-dimethylimidazo[2,1-b]quinazoline or a pharmaceutically acceptable salt thereof.

16. The compound of claim 1, which is 5,10-dihydro-8,9-dimethylimidazo[2,1-b]quinazoline or a pharmaceutically acceptable salt thereof.

17. The compound of claim 1, which is 5,10-dihydro-9-methoxyimidazo[2,1-b]quinazoline or a pharmaceutically acceptable salt thereof.

18. The compound of claim 1, which is 5,10-dihydro-7-methoxyimidazo[2,1-b]quinazoline or a pharmaceutically acceptable salt thereof.

19. The compound of claim 1, which is 5,10-dihydro-6-methoxyimidazo[2,1-b]quinazoline or a pharmaceutically acceptable salt thereof.

20. The compound of claim 1, which is 5,10-dihydro-8-methoxyimidazo[2,1-b]quinazoline or a pharmaceutically acceptable salt thereof.

21. The compound of claim 1, which is 5,10-dihydro-7,8-dihydroxyimidazo[2,1-b]quinazoline or a pharmaceutically acceptable salt thereof.

22. The compound of claim 1, which is 5,10-dihydro-9-hydroxyimidazo[2,1-b]quinazoline or a pharmaceutically acceptable salt thereof.

23. The compound of claim 1, which is 5,10-dihydro-7-hydroxyimidazo[2,1-b]quinazoline or a pharmaceutically acceptable salt thereof.

24. The compound of claim 1, which is 5,10-dihydro-5-phenylimidazo[2,1-b]quinazoline or a pharmaceutically acceptable salt thereof.

25. The compound of claim 1, which is 5,10-dihydro-5-methylimidazo[2,1-b]quinazoline or a pharmaceutically acceptable salt thereof.

* * * * *